United States Patent

Ehr et al.

[11] Patent Number: 6,102,497
[45] Date of Patent: Aug. 15, 2000

[54] UNIVERSAL CART

[75] Inventors: Chris J. Ehr, Longmont; Valintina S. Arroyo, Erie; Vernita Kelm, Lafayette; Karl D. Roberts, Jr., Broomfield, all of Colo.; Brady Austin Olason, Edmonds, Wash.; Sohrab Vossoughi, Portland; James N. Grant, Newberg, both of Oreg.

[73] Assignee: Sherwood Services AG, Schaffhausen, Switzerland

[21] Appl. No.: 09/184,909

[22] Filed: Nov. 3, 1998

[51] Int. Cl.[7] ................................................. A47B 81/00
[52] U.S. Cl. .................. 312/209; 312/249.13; 280/47.35
[58] Field of Search ................................ 312/209, 257.1, 312/249.1, 249.8, 249.11, 249.12, 249.13, 223.3, 108; 108/92, 53.5; 280/47.35, 79.2, 79.3, 47.34

[56] References Cited

U.S. PATENT DOCUMENTS

| | | | |
|---|---|---|---|
| 1,961,394 | 6/1934 | Rothe | 280/47.35 X |
| 2,590,285 | 3/1952 | Wiltshire | 280/47.35 X |
| 2,673,671 | 3/1954 | Williams | 280/47.35 X |
| 2,682,932 | 7/1954 | Howard | 312/209 |
| 3,523,694 | 8/1970 | Oliver | 108/53.5 X |
| 3,777,673 | 12/1973 | Blazey et al. | 312/209 X |
| 3,788,662 | 1/1974 | Rasmussen et al. | 280/79.2 X |
| 3,822,924 | 7/1974 | Lust | 312/108 X |
| 3,997,218 | 12/1976 | Wolf et al. | 312/209 |
| 4,108,514 | 8/1978 | Zimmerman | 312/108 X |
| 4,114,965 | 9/1978 | Oye et al. | 312/209 |
| 4,474,416 | 10/1984 | Rogahn | 312/249.13 X |
| 4,673,092 | 6/1987 | Lamson et al. | 108/53.5 X |
| 4,681,378 | 7/1987 | Hellman, III | 312/108 |
| 4,998,023 | 3/1991 | Kitts | 280/47.35 |
| 5,016,948 | 5/1991 | Welch et al. | 312/257.1 X |
| 5,041,110 | 8/1991 | Fleenor . | |
| 5,205,630 | 4/1993 | Welch et al. | 312/249.11 |
| 5,292,029 | 3/1994 | Pearson | 312/209 X |
| 5,330,469 | 7/1994 | Fleenor . | |
| 5,399,007 | 3/1995 | Marconet | 312/209 |
| 5,405,587 | 4/1995 | Fernandez et al. | 312/209 X |
| 5,427,394 | 6/1995 | Lauto | 280/47.35 |
| 5,445,397 | 8/1995 | Evans | 280/47.18 |
| 5,518,310 | 5/1996 | Ellman et al. | 312/249.12 |
| 5,662,644 | 9/1997 | Swor . | |
| 5,674,218 | 10/1997 | Rubinsky et al. . | |
| 5,695,205 | 12/1997 | Liu | 280/47.35 X |

FOREIGN PATENT DOCUMENTS

| | | | |
|---|---|---|---|
| 3316896 | 11/1984 | Germany | 280/47.35 |
| 6009021 | 1/1994 | Japan | 280/47.35 |
| 8011722 | 1/1996 | Japan . | |

*Primary Examiner*—Peter M. Cuomo
*Assistant Examiner*—James O. Hansen

[57] ABSTRACT

A cart for supporting various types of medical equipment including a main support shelf, a bottom support shelf and a pair of support legs. Each support leg having a first end attached to the main support shelf and a second end attached to the bottom shelf. The cart also including an upper support shelf which couples in spaced relation to the main support shelf. Additional support shelves can be selectively mounted and stacked atop the main support shelf in a similar fashion.

8 Claims, 4 Drawing Sheets

UNIVERSAL CART

TECHNICAL FIELD

The present disclosure relates to carts used for supporting medical equipment. More particularly, the present disclosure relates to a medical equipment cart having a main shelf, a bottom shelf and at least one selectively mountable upper shelf all designed to support various types of medical equipment.

BACKGROUND OF RELATED ART

Carts for supporting various types of medical equipment, e.g., electrosurgical generators, lasers and laser peripherals, endoscopic instruments, coagulators, etc., are well known in the art (See for example, U.S. Pat. Nos. 4,681,378 to Hellmann, III, 5,016,948 to Welch et al., 5,041,110 to Fleenor, 5,292,029 to Pearson, 5,330,469 to Fleenor, 5,427,394 to Lauto, and 5,518,310 to Ellman et al.). However, the majority of these carts are one piece units which are typically designed for one or perhaps a specific combination of medical instruments. Still other carts are designed for specific medical purposes and include various features which are integrated into the cart's design, e.g., flow valves, foot switches, gas tubing, display panels, laser housings, etc.

Since many of these prior art carts have sophisticated electronic and mechanical components integrally designed into their respective housings and frames, it is often impractical to use these carts for supporting other or additional medical equipment. Moreover, the majority of these carts are not designed to support and secure different types of medical equipment. At most, an additional piece medical equipment could be placed atop the cart or perhaps atop another piece of medical equipment.

While generally acceptable for their intended purposes, the prior art carts are complicated and expensive. Accordingly, the need exists for a new, effective and inexpensive medical cart for supporting various types of medical equipment.

SUMMARY

The present disclosure relates to a cart for supporting medical equipment which includes a main support shelf, a bottom support shelf and at least one support leg having a first end which is attached to and which depends from the main support shelf and having a second end which is attached to the bottom shelf. The cart also includes at least one upper shelf which selectively mounts in spaced relation atop the main support shelf.

Two support legs can be attached to and can depend from opposing side edges of the main support shelf. Preferably, the support legs are attached to the main support shelf proximate the center of gravity of the cart and each of the support legs depends from the main support shelf in an angular fashion towards the bottom shelf. The upper shelf can include a pair of side support members which align with and couple to each of the support legs of the main support shelf such that the upper shelf mounts in spaced relation atop the main support shelf. Preferably, the side support members of the upper shelf telescopically couple to the support legs. A plurality of spacers can be employed to mount the medical equipment within a corresponding plurality of grooves disposed within one of the shelves. Casters can be attached to the bottom shelf and the cart can be equipped with a handle to facilitate transporting the cart and the medial equipment mounted thereon.

DETAILED DESCRIPTION OF THE PREFERRED EMBODIMENTS

Figure 1:
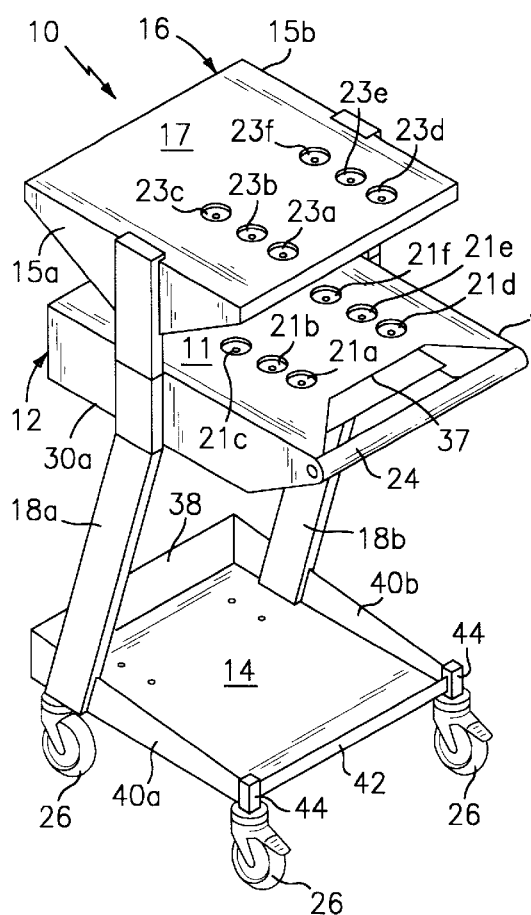
FIG. 1 is a front perspective view of a medical cart according to the present disclosure.
Figure 2:
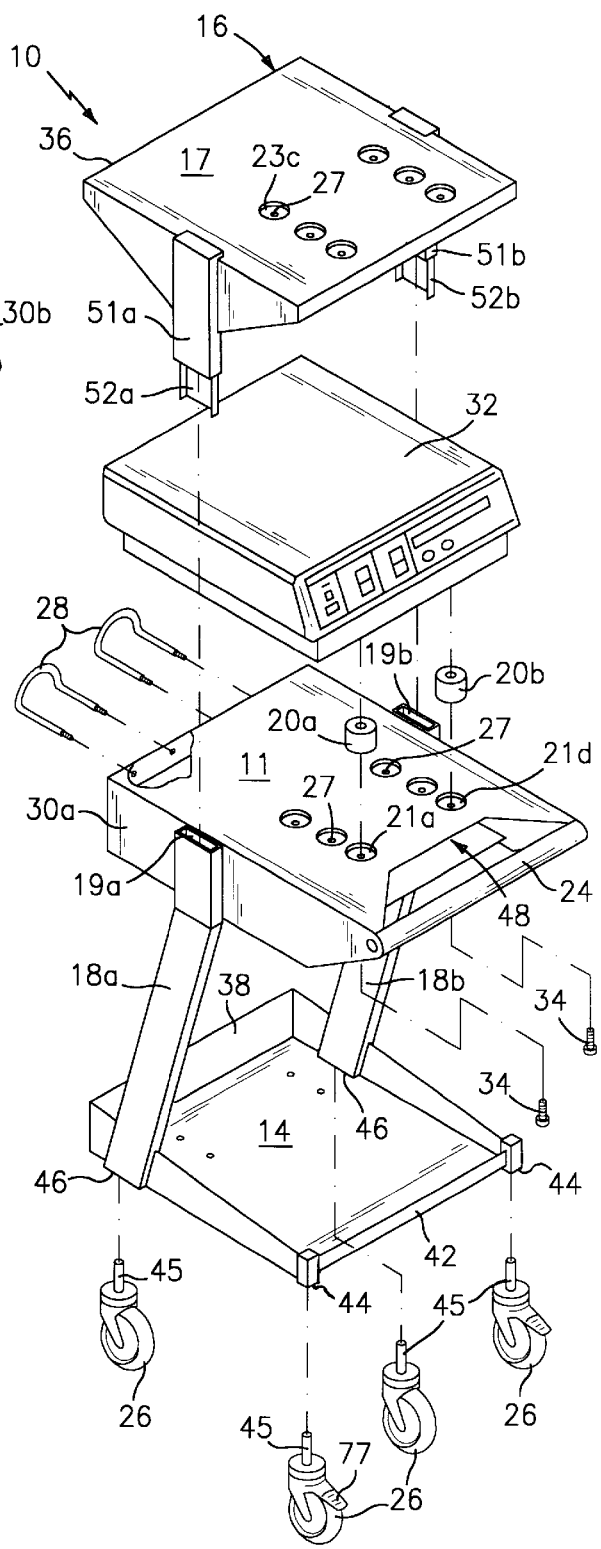
FIG. 2 is front, perspective, exploded view of the medical cart of FIG. 1 with a generator positioned thereon.

Referring now to FIGS. 1 and 2, a medical cart is shown according to the present disclosure generally identified by reference numeral 10. Cart 10 includes a main support shelf 12 which is defined by a top plate 11, two opposing side edges 30a and 30b, front edge 37 and rear edge 33. Cart 10 also includes a bottom support shelf 14 and an upper support shelf 16 which is selectively mountable atop main support shelf 12.

As shown best in FIG. 1, main support shelf 12 has a pair of opposing support legs 18a and 18b which are attached at either side edge 30a, 30b of the main support shelf 12 and which depend in an angularly fashion downwardly therefrom. The opposite end of each support leg 18a, 18b integrally mates with the side edges 40a and 40b of the bottom shelf 14 preferably near the rear edge 38 thereof. In some cases, however, it may be preferable to attach the support legs 18a, 18b proximate the forward edge 42 of the bottom shelf 14 to suit a particular purpose.

Alternatively, the lower portion of each support leg 18a, 18b may be bifurcated and attached proximate the rear and forward edges 38, 42 of the bottom shelf 14. Attaching the legs 18a, 18b in this fashion may provide greater stability for the cart 10. Advantageously, each support leg 18a, 18b is attached to the main support shelf 12 near the center of each side edge 30a, 30b such that the main support shelf 12 is supported proximate the cart's center of gravity. This may also increase the overall stability of the cart 10.

As best illustrated in FIGS. 1 and 2, top plate 11 of the main support shelf 12 includes a plurality of generally circular grooves 21a–21c and 21d–21f located thereon which each have a central bore 27 extending therethrough. Preferably, grooves 21a–c and 21d–f are dimensioned to releasably engage and secure a set of corresponding spacers 20a, 20b which are mounted to the medical equipment, e.g., electrosurgical generator 32. These spacers have some shock absorbing qualities as well. More particularly and as best shown in the exploded view of FIG. 2, screws 34 are inserted through bores 27 in a set of grooves, e.g., 21a, 21d, and through spacers 20a, 20b to engage the underside of generator 32 and secure the generator 32 to shelf 12. Spacers 20a, 20b are preferably configured to align with and recess within the set of grooves 21a, 21d.

Grooves, e.g., 21a–c and 21d–f are pre-aligned within shelf 12 so as to mountingly engage corresponding spacers 20a, 20b affixed to specific types of medical equipment. For example, one particular embodiment of the medical cart 10 includes three sets of grooves 21a and 21d, 21b and 21e, and 21c and 21f located within shelf 12 which are each specifically dimensioned and aligned to engage corresponding spacers affixed to the underside of various medical equipment sold by VALLEYLAB®, a subdivision of United States Surgical Corporation located at 5920 Longbow Drive, Boulder, Colo. 80301-3299 (i.e., groove pair 21a and 21d is aligned to mount VALLEYLAB®'s ARGON II™, F300™, FORCE EZ™ and OPTIMUMM™ instruments; groove pair 21b and 21e is aligned to mount VALLEYLAB®'s FORCE 1C™, LIGASURE™ and VESTA™ instruments; and groove pair 21c and 21f is aligned to mount VALLEYLAB®'s FORCE 2™ and FORCE FX® instruments). It is contemplated that the grooves 21a–c and 21d–f can be arranged with shelf 12 in any manner to securely mount a particular piece of medical equipment.

Preferably, the upper support shelf 16 is generally rectangular and includes a top plate 17 and a pair of opposing side edges 15a, 15b which depend therefrom. Upper shelf 16 can also contain a series of pre-aligned grooves 23a, 23b which engage with pre-aligned spacers 20a, 20b and releasably engage additional medical equipment in the same or similar manner as described above with respect to the main support shelf 12. For example, the grooves of the upper shelf 16 of VALLEYLAB®'s medical cart can also be specifically dimensioned and aligned to receive the same above-mentioned instruments sold by VALLEYLAB®.

As best seen in FIG. 2, a side support member 51a and 51b is integral with each side edge 15a, 15b and depends downwardly therefrom. Each side support member 51a, 51b is dimensioned to releasably engage a corresponding support leg 18a, 18b, respectively, such that upper shelf 16 mounts in spaced relation atop main support shelf 12. Additional auxiliary shelves can be mounted in a similar manner such that multiple pieces of medical equipment can be supported in a stack-like manner.

In the particular embodiment shown in FIG. 2, each support leg 18a, 18b is hollow such that openings 19a and 19b are created in each leg 18a, 18b. Preferably, each side member 51a, 51b includes a pair of generally rectangular flanges 52a and 52b, respectively, which depend therefrom and which telescopically engage openings 19a, 19b. Both flanges 52a, 52b and openings 19a, 19b are configured and dimensioned to facilitate easy slideable telescopic movement. Preferably, side members 51a, 51b each depend from side edges 15a, 15b near the center of shelf 16 such that shelf 16 is supported proximate the cart's center of gravity.

In one particular embodiment of the cart 10, a plurality of wheels or casters 26 are mounted to the bottom shelf 14 to facilitate transport of the medical cart 10 and the equipment mounted thereon. As best seen in FIGS. 1 and 2, the forward edge 42 of bottom shelf 14 includes a pair of ports 44 each for receiving a portion 45 of one of the casters 26. Preferably, the bottom distal end of each side support member 18a, 18b is designed to receive portion 45 to secure the rear casters 26 to the cart 10. Alternatively, the rear casters 26 may be mounted to the rear edge 38 of the bottom shelf through an additional pair of ports 46 in the same or similar fashion as the forward casters 26. The casters 26 may either be mounted for rotation about an axis perpendicular to the bottom of shelf 14, or, in the alternative, one or more of the casters 26 may be fixed from rotation for improved directional stability of the cart 10. Preferably, casters 26 include known locking mechanisms 77 to prevent undesired movement of the cart 10.

Figure 3:
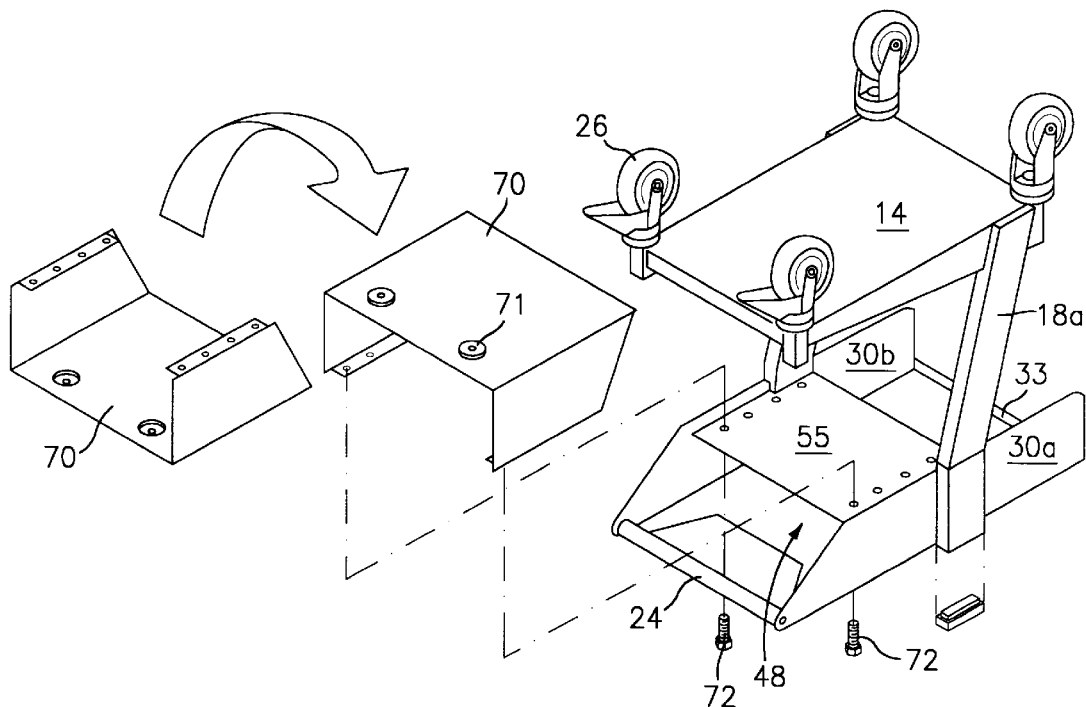
FIG. 3 is an upside-down, perspective, partially-exploded view of an alternate embodiment of the present disclosure showing the mounting position of an optional shelf.
Figure 4:
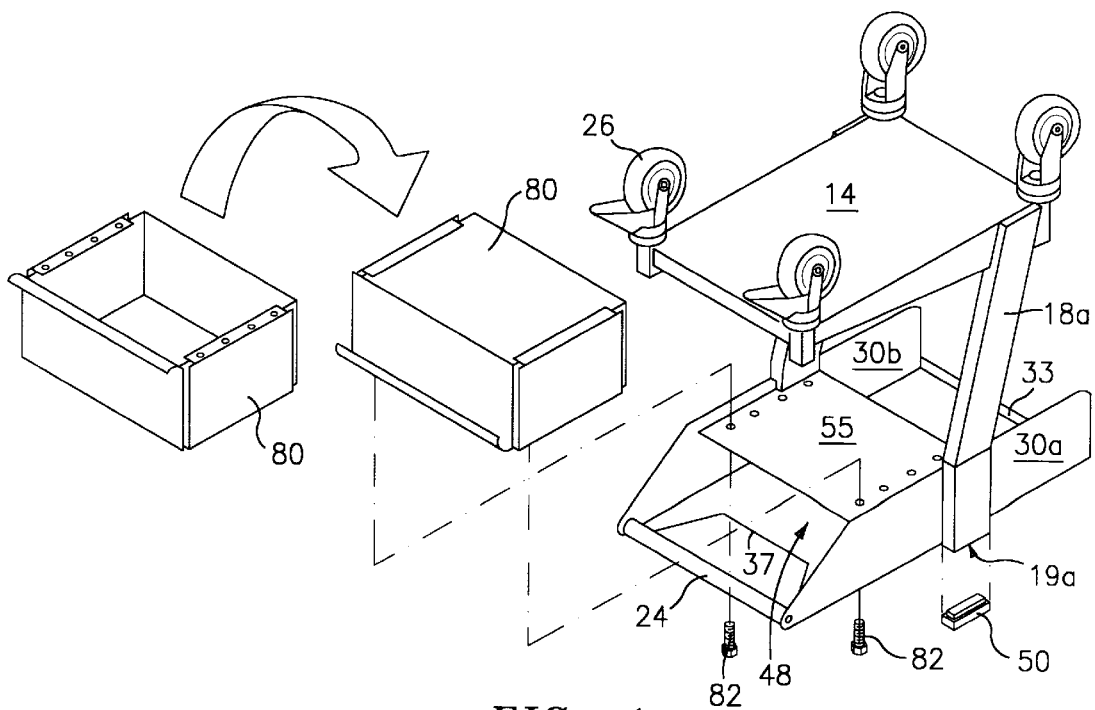
FIG. 4 is an upside-down, perspective, partially-exploded view of an alternate embodiment of the present disclosure showing the mounting position of an optional drawer.
Figure 5:
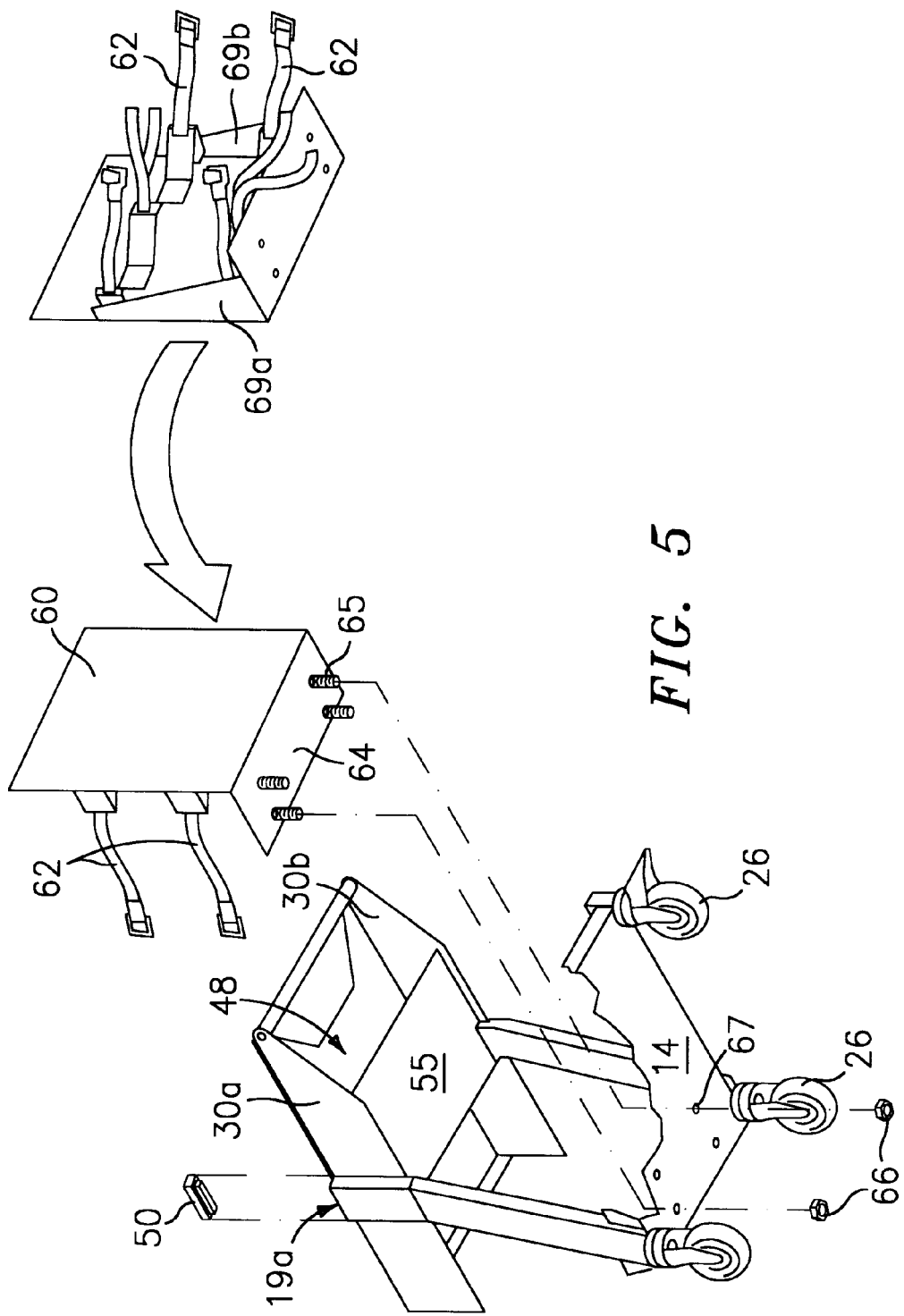
FIG. 5 is a bottom, perspective, partially-exploded view of an alternate embodiment of the present disclosure showing the mounting position of an optional tank panel.

As seen best in FIGS. 3–5, a bottom panel 55 is attached between the depending side edges 30a, 30b in spaced relation to main support shelf 12 to define an access 48 therebetween. Preferably, an optional accessory shelf 70 can be selectively mounted to panel 55 by fasteners 72 to store and/or support additional medical equipment, operational manuals or supplies. In much the same manner, an optional drawer 80 can be selectively mounted to panel 55 by fasteners 82 for the same or similar purpose.

Figure 6:
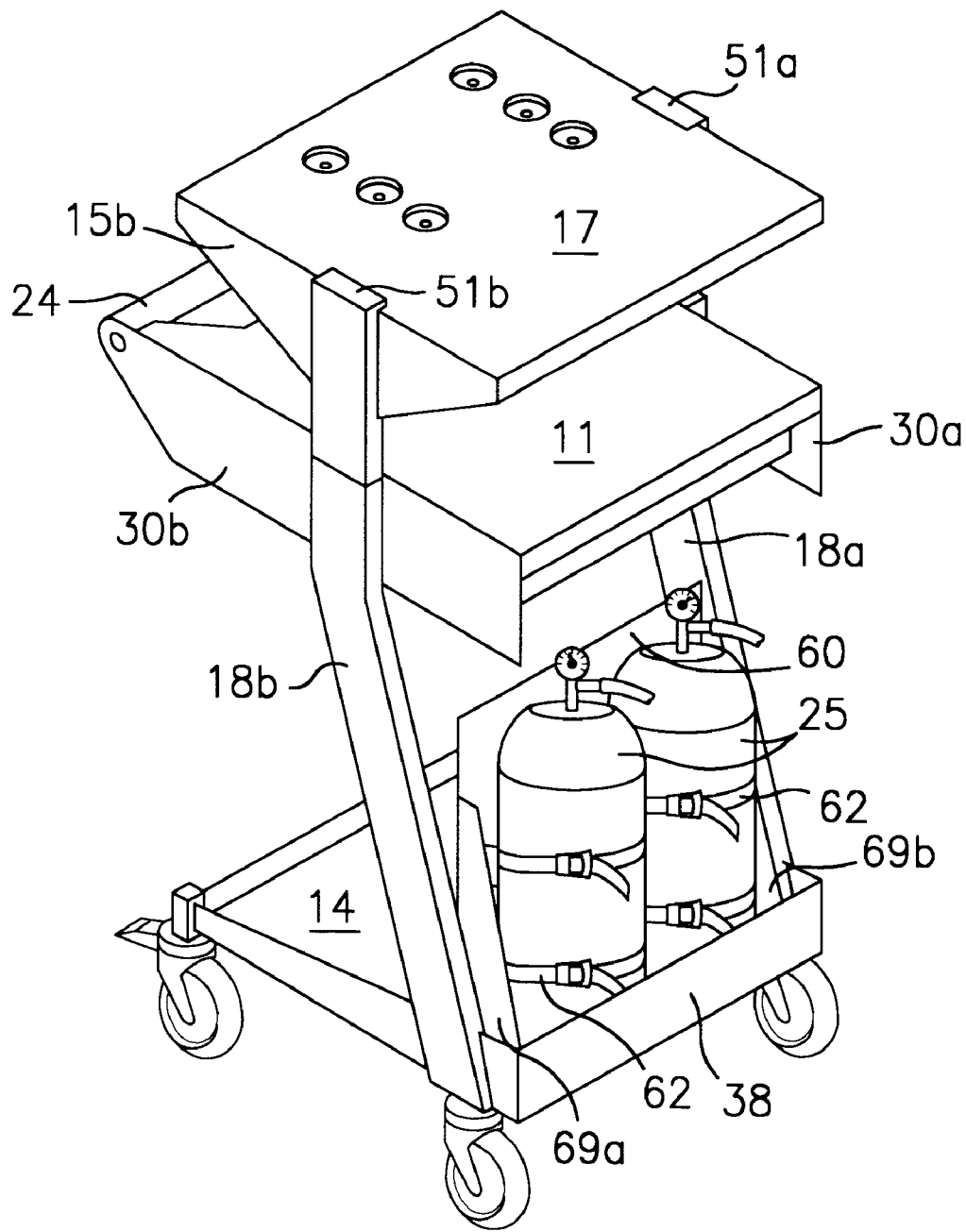
FIG. 6 is rear, perspective view of the FIG. 5 embodiment showing the a pair of gas tanks supported on the bottom shelf of the medical cart.

FIGS. 5 and 6 show a tank support panel 60 which can be selectively mounted atop bottom shelf 14 to support and/or secure one or more gas containers or tanks 25 (FIG. 6), e.g., argon gas containers. Tank support panel 60 includes bottom flange 64 which projects perpendicularly from panel 60 and a pair of opposing side flanges 69a, 69b. Preferably, flange 64 includes a plurality of fasteners 65 which depend therefrom and which align with a corresponding plurality of screw holes 67 located in the bottom shelf 14 which cooperate to secure panel 60 to cart 10. Nut 66 engages fastener 65 to further secure panel 60 to cart 10. However, in some cases it may be preferable to attach panel 60 to cart 10 in a different manner, e.g., snap-fit engagement or welding. Panel 60 also includes straps 62 for securing tanks 25 to panel 60.

In another embodiment, cart 10 includes a bar or handle 24 which mounts to the main support shelf 12. Preferably, the side edges 30a, 30b project forwardly from the front edge 37 of the main support shelf 12 such that bar 24 can be mounted between the opposing edges 30a, 30b. In the particular embodiment shown in FIGS. 1–5, front edge 37 is recessed or tapered inwardly to accommodate handle 24. In some cases, however, it may be preferable to mount the handle 24 in different fashion, e.g., atop main support shelf 12, or, alternatively, the main support shelf 12 may be manufactured with a handle 24 formed therein.

Preferably, cart 10 also includes a series of cord management hooks 28 which are selectively attachable to various parts of the cart 10, e.g., rear edges 33, 36 and 38 of shelves 12, 16 and 14, respectively. As can be appreciated, cord hooks 28 are specifically designed for simple and quick attachment to the various parts of the cart 10 so as to organize and arrange stray electrical cords leading from the medical equipment. Advantageously, more than one cord hook 28 can be employed on one or more shelves depending-upon the number of electrical cords involved.

Preferably, cart 10 also includes a pair of end caps 50 which engage openings 19a, 19b, respectively, when the upper support shelf 16 is not mounted atop the main support shelf 12.

From the foregoing and with reference to the various figure drawings, those skilled in the art will appreciate that certain modifications can be made without departing from the scope of the present disclosure. For example, while the main support shelf 12 and other shelves 14 and 16 have generally been shown to be rectangular in construction, the shelves can be designed in any shape depending upon the particular instruments involved, e.g., round, ovoid, polygonal, etc.

In the particular embodiments shown in the figures, the upper shelf 16 is telescopically mounted atop the main support shelf 12, however, in some cases it may be preferable to mount the upper shelf 16 in a different manner, e.g., snap-fit, tongue and groove and/or ratchet and pawl. Moreover, although the figures depict the equipment being anchored to the cart by screws, other methods of attachment may be employed, e.g., locking dials, clasps and/or latches.

Although the particular figures depict only one upper support shelf 16 mounted atop the main support shelf 12, any number of auxiliary shelves can be mounted in a similar fashion to support additional medical equipment.

There have been described and illustrated herein several embodiments of a medical cart for supporting various pieces of medical equipment. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplications of preferred embodiments. Those skilled in the art will envision other modifications within the scope and spirit of the claims appended hereto.

What is claimed is:

1. A cart for supporting medical equipment, comprising:
    a main support shelf having a pair of opposing side edges, a front edge and a rear edge, said main support shelf having a plurality of generally circular, pre-aligned grooves each having a central bore located therethrough, each of said grooves being dimensioned to releasably engage a corresponding spacer mounted to said medical equipment;
    a bottom support shelf having a forward edge and a rear edge;
    a pair of support legs each having a first end which is attached proximate the center of each side edge and a second end which is attached proximate said rear edge of said bottom shelf such that said support leg depends from the center of each support leg at an angle other than ninety degrees towards said rear edge of said bottom shelf; and
    at least one upper shelf which telescopically couples to said main support shelf such that said main support shelf and said upper support shelf are disposed in spaced relation relative to one another.

2. A cart according to claim 1 further comprising at least one caster attached to said bottom shelf.

3. A cart according to claim 1 wherein at least one of said shelves further comprises a handle for moving said cart.

4. A cart according to claim 1 wherein said cart further comprises at least one hook for organizing electrical cords.

5. A cart according to claim 4 wherein said at least one hook is selectively positionable in a plurality of positions on the cart.

6. A cart according to claim 1 further comprising an accessory drawer selectively attached between said main support shelf and said bottom shelf.

7. A cart according to claim 1 further comprising a support panel selectively attached to said bottom shelf for supporting at least one gas container.

8. A cart according to claim 1 further comprising an accessory shelf selectively attached between said main support shelf and said bottom shelf.

* * * * *